(12) United States Patent
Bermejo Oses et al.

(10) Patent No.: US 7,951,769 B2
(45) Date of Patent: May 31, 2011

(54) NON-RINSE FABRIC SOFTENER

(75) Inventors: Maria Jose Bermejo Oses, Barcelona (ES); Blanca Nogues Lopez, Barcelona (ES)

(73) Assignee: Kao Corporation, S.A., Barcelona (ES)

( * ) Notice: Subject to any disclaimer, the term of this patent is extended or adjusted under 35 U.S.C. 154(b) by 145 days.

(21) Appl. No.: 12/521,697

(22) PCT Filed: Nov. 9, 2007

(86) PCT No.: PCT/EP2007/062156
§ 371 (c)(1),
(2), (4) Date: Jun. 29, 2009

(87) PCT Pub. No.: WO2008/080680
PCT Pub. Date: Jul. 10, 2008

(65) Prior Publication Data
US 2010/0331231 A1     Dec. 30, 2010

(30) Foreign Application Priority Data
Dec. 28, 2006  (EP) .................................. 06380339

(51) Int. Cl.
*C11D 1/835* (2006.01)
(52) U.S. Cl. ..................................................... 510/504
(58) Field of Classification Search .................. 510/504
See application file for complete search history.

(56) References Cited

U.S. PATENT DOCUMENTS

| | | | |
|---|---|---|---|
| 6,458,343 B1 * | 10/2002 | Zeman et al. | 424/63 |
| 6,949,500 B2 * | 9/2005 | Salesses et al. | 510/475 |
| 2002/0025915 A1 | 2/2002 | Franklin et al. | |
| 2004/0097395 A1 * | 5/2004 | Crutzen | 510/515 |
| 2004/0097396 A1 * | 5/2004 | Peeters et al. | 510/515 |
| 2004/0116321 A1 * | 6/2004 | Salesses et al. | 510/515 |
| 2004/0116322 A1 * | 6/2004 | Yianakopoulos et al. | 510/515 |
| 2006/0030516 A1 | 2/2006 | Demeyere et al. | |

FOREIGN PATENT DOCUMENTS

| | | |
|---|---|---|
| EP | 1 103 650 A1 | 5/2001 |
| WO | WO 01/32813 A1 | 5/2001 |
| WO | WO 2006/113658 A2 | 10/2006 |

\* cited by examiner

*Primary Examiner* — John R Hardee
(74) *Attorney, Agent, or Firm* — Edward W. Grolz, Esq.

(57) ABSTRACT

The invention relates to compositions which are suitable as fabric softeners, particularly for softening fabrics that have been washed with highly concentrated detergents. Said compositions are obtainable by esterification of a $C_6$-$C_{22}$ fatty acid with triethanolamine and subsequent quaternization, said compositions containing non-quaternized di-esteramine, non-quaternized tri-esteramine, quaternized mono-esteramine, quaternized di-esteramine and quaternized tri-esteramine, wherein the weight ratio of non-quaternized tri-esteramine to quaternized tri-esteramine is higher than 1.5.

13 Claims, No Drawings

NON-RINSE FABRIC SOFTENER

TECHNICAL FIELD

The invention relates to compositions which are suitable as fabric softeners, particularly for softening fabrics that have been washed with highly concentrated detergents.

PRIOR ART

Fabric care compositions deliver a number of desirable characteristics to fabrics upon treatment, including an improved fabric feel and a perception of freshness. However, in order to secure high consumer acceptance of any fabric care composition, it is essential to provide consumer-desirable product aesthetics, for example not only an appealing neat product odor and a pleasant product color, but especially an appropriate product rheology and satisfactory physical product stability. Controlling the rheology of the fabric care composition becomes increasingly challenging as the concentration of the fabric softening active is lowered (i.e., dilute).

The fabric softener is generally added to the fabric after the washing process and subsequent rinsing. However, there may be some carry-over of anionic surfactants to the step of adding the fabric softener, particularly when the ratio of detergent to water is high in the washing step, which is the case for example under hand washing conditions or in the case of washing in top loading non-automatic washing machine treatments. This carry-over of anionic surfactants may present problems with regard to the subsequent softener treatment since the fabric softener actives may interact with the residual anionic surfactants. For example, this interaction may result in a reduced softening effect.

WO-A-02072745 describes rinse added composition for the conditioning of fabric in a rinse, whereby the composition comprises a fabric softener active, a suds suppressing system and a surfactant scavenger, characterized in that the composition has a suds reduction value of at least about 90% and is free from visible flocs when used in the presence of residual detergent surfactant. According to WO-A-02072745, it is preferred that the fabric softener active and the surfactant scavenger derive from the same starting material, being the fabric softener active a di-alkyl substituted quaternary ammonium compound and the surfactant scavenger a mono-alkyl quaternary ammonium compound, because they can be produced together in a single chemical reaction and, in this way, final composition is less likely to experience phase separation.

According to WO-A-02072745, if the molar ratio of fatty acid to amine is less than 2:1, preferably between 1.6:1 to 0.8:1, and more preferably between 1.6:1 and 1:1, a mixture of mono- and di-alkyl substituted compounds is obtained.

Preferred fabric softener actives according to WO-A-02072745 are esterquats such as N,N-bis(stearoyl-oxy-ethyl) N,N-dimethyl ammonium chloride, N,N-bis(tallowoyl-oxy-ethyl) N,N-dimethyl ammonium chloride, N,N-bis(stearoyl-oxy-ethyl) N-(2-hydroxyethyl) N-methyl ammonium methylsulfate or 1,2-di(stearoyl-oxy)-3-trimethyl ammoniumpropane chloride.

Preferred surfactant scavengers are the mono-alkyl variant of the fabric softener active (mono-alkyl esterquat).

There is an abundant bibliography on the subject of combining dialkyl substituted quaternary ammonium compounds and monoalkyl quaternary ammonium compounds, amongst which patents or patent applications EP-A-0018039, EP-A-0369500, U.S. Pat. No. 4,360,437 or U.S. Pat. No. 4,855,072 amongst many others, may be mentioned.

References describing mixtures of dialkyl substituted esterquats and monoalkyl esterquats are WO-A-9414935, WO-A-9742279, WO-A-2004044113 amongst many others.

U.S. Pat. No. 6,737,392 describes a fabric softener composition containing a blend of high monoalkyl methyldiethanolamine and triethanolamine esterquats. The fabric softener composition includes a blend of from 15 to 65%, by weight of the total blend, of a triethanolamine esterquat and from 35 to 85%, by weight of the total blend, of a methyldiethanolamine esterquat having a monoalkyl esterquat level of about 10% or greater. According to U.S. Pat. No. 6,737,392, the preferred molar ratio of fatty acid to methyldiethanolamine is between 1.2:1 to 1.7:1, preferably between 1.2:1 and 1.5:1, more preferably between 1.2:1 to 1.35:1 in order to increase the level of monoalkyl esterquat.

Finally, according to F. E. Friedli et. at., in "Upgrading triethanolamine esterquat performance to new levels", Journal of Surfactants and Detergents, Vol. 5, No. 3 (July 2002), published by the AOCS, using a fatty acid/triethanolamine molar ratio of 2:1, a final product mixture containing mono-esterquat, di-esterquat, tri-esterquat and tri-esteramine is obtained. The typical weight percent analysis for commercial triethanolamine esterquat is 23% mono-esterquat, 47% di-esterquat, 19% tri-esterquat and 11% tri-esteramine.

SUMMARY OF THE INVENTION

It is the problem underlying the present invention to provide a new composition that is suitable for use as a fabric softener, particularly in the presence of anionic surfactants that may be carried over from the washing process, and a process for its production.

This problem is solved by the provision of a composition comprising a quaternary ammonium salt mixture which is obtainable by esterification of a $C_6$-$C_{22}$ fatty acid with triethanolamine and subsequent quaternization, said mixture containing non-quaternized di-esteramine, non-quaternized tri-enteramine, quaternized mono-enteramine, quaternized di-esteramine and quaternized tri-esteramine, wherein the weight ratio of non-quaternized tri-esteramine to quaternized tri-esteramine is higher than 1.5.

This composition can be produced by a process comprising the condensation of $C_6$-$C_{22}$ fatty acids with triethanolamine providing an esteramine mixture comprising mono-esteramine, di-esteramine, and tri-esteramine, quaternization of said mixture with alkylating agents, wherein the molar ratio of alkylating agent to esteramine ranges from 0.6 to 0.9, preferably from 0.65 to 0.85.

DETAILED DESCRIPTION OF THE INVENTION

The Esterquat

Esterquats are generally understood to be quaternized fatty acid alkanolamine ester salts which, in recent years, have proven to be suitable as another group of cationic surfactants—besides the known tetraalkyl ammonium salts—for use as fabric softeners and as conditioners for cosmetics. They are normally produced by esterification of fatty acids with alkanolamines and subsequent quaternization of the alkanolamine esters with methyl chloride or dimethyl sulfate. Reference is made in this connection to WO-A-9101295. The esterquats of the present invention are obtainable by esterification of a $C_6$-$C_{22}$ fatty acid with triethanolamine and subsequent quaternization, said mixture containing non-quaternized di-esteramine (di-esteramine), non-quaternized tri-esteramine (tri-esteramine), quaternized mono-esteramine (mono-esterquat), quaternized di-esteramine (di-esterquat) and quaternized tri-esteramine (tri-esterquat), wherein the weight ratio of non-quaternized tri-esteramine to quaternized tri-esteramine is higher than 1.5. In the following, the two steps in the synthesis of the esterquat are described in more detail.

The Esterification

According to the invention, the alkanolamine esters can be obtained by the condensation of $C_6$-$C_{22}$ fatty acids with triethanolamine (TEA).

Examples of suitable $C_6$-$C_{22}$ fatty acids are those obtained from vegetable and animal oils and fats such those obtained from castor oil, coconut oil, corn oil, mustard oil, olive oil, palm oil, peanut oil, rapeseed oil, sunflower oil, soybean oil, tall oil, tallow, eventually totally or partially hydrogenated, as well as purified or synthetic fatty acids, like caproic acid, caprylic acid, capric acid, isotridecanoic acid, lauric acid, myristic acid, palmitic acid, palmoleic acid, stearic acid, isostearic acid, 2-ethylhexanoic acid, oleic acid, elaidinic acid, petroselenic acid, linoleic acid, linolenic acid, eleostearic acid, ricinoleic acid, arachidic acid, gadoleic acid, behenic acid, erucic acid, or their technical-grade mixtures.

The fatty acid is preferably a $C_8$-$C_{18}$ acid containing a degree of unsaturation such that the iodine value ("IV") is in the range from 0-90, preferably from 10-90, more preferably in the range from 15-85, most preferably 15-55.

It is also preferred that the fatty acid(s) employed in the present process have a cis to trans isomer ratio from 80:20 to 95:5. More preferably, the trans isomer content of said fatty acid(s) is less than 10%. An optimum trans-isomer content is between 0.5-5%.

The esterification of $C_6$-$C_{22}$ fatty acids with triethanolamine (TEA) can be carried out by known methods, such as it is described in WO-A-9101295.

It is preferred that the esterification of the $C_6$-$C_{22}$ fatty acids with triethanolamine is carried out at a temperature of between 120° C. and 220° C., for a period of from 2 to 10 hours, preferably at a reduced pressure of 5 to 200 mbar and in the presence of some of the catalysts already known for the esterification, for example, hypophosphorous acid and para-toluene sulphonic acid, and also in the presence of some of the usual stabilizers and antioxidants such as tocopherols, BHT, BHA, citric acid, etc.

The molar ratio of the $C_6$-$C_{22}$ fatty acids to triethanolamine is generally in the range 1.5:1 to 2.5:1, more from 1.6:1 to 2.0:1.

The reaction product of the esterification reaction is a complex mixture of mono-, di- and tri-esters of fatty acids, namely a mixture of mono-enteramine, di-esteramine, and tri-enteramine, besides non-reacted species. The mono-esteramine, di-esteramine, and tri-esteramine have the following formulae (II) to (IV):

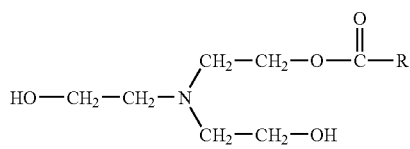

(II)

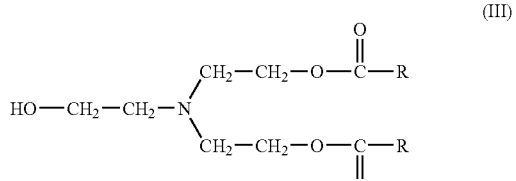

(III)

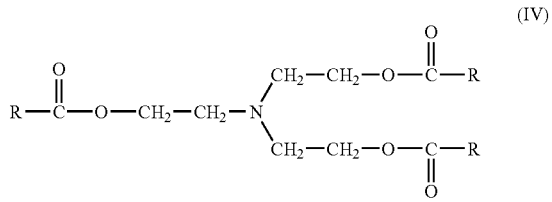

(IV)

In the above formulae R represents a $C_5$-$C_{21}$ hydrocarbon group.

The Quaternization

The quaternization of the reaction product of the esterification reaction may be carried out in a known manner, such as it is described in WO-A-9101295. Preferred alkylating agents include $C_1$-$C_3$ straight or branched chain alkyl halides, phosphates, carbonates, or sulfates, $C_7$-$C_{10}$ aralkyl halides, phosphates or sulfates, and mixtures thereof. Examples of preferred alkylating agents include but are not limited to methyl chloride, benzyl chloride, diethyl sulfate, dimethyl carbonate, trimethyl phosphate, dimethyl sulfate or mixtures thereof. Choosing the type and amount of alkylating agent employed is known for the skilled in the art. According to the present invention, the molar ratio alkylating agent to enteramine generally ranges from 0.6 to 0.9, preferably from 0.65 to 0.85, even more preferably from 0.7 to 0.83.

The quaternization may be carried out in bulk or in solvent, at temperatures ranging from 55° C.-120° C. If a solvent is employed, then the starting materials and/or product must be soluble in the solvent to the extent necessary for the reaction.

The resulting quaternized composition (i.e. the esterquat) contains, besides non-quaternized di-esteramine, non-quaternized triesteramine and possibly non-quaternized mono-esteramine besides other by products, mono-esterquat, di-esterquat, and tri-esterquat of the following formulae V to VII, respectively:

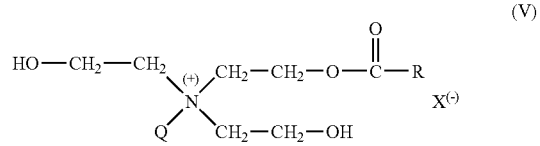

(V)

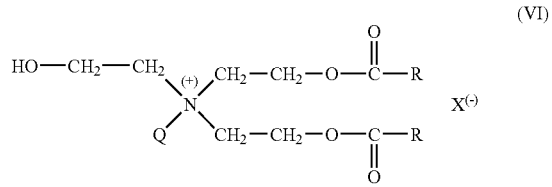

(VI)

-continued

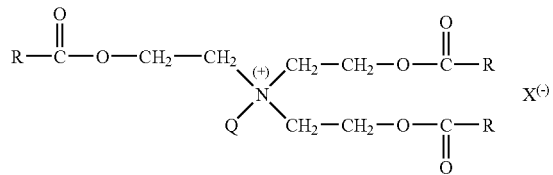

wherein

R has the same meanings as in Formulae II to IV,

X represents a softener compatible anion, preferably chloride, bromide, methyl sulfate, ethyl sulfate and nitrate, more preferably chloride or methyl sulfate, and Q is a $C_1$-$C_3$ alkyl group.

In the resulting esterquat, the weight ratio of (non-quaternized) tri-esteramine to tri-esterquat is at least 1.5, more preferably at least 3, even more preferably at least 5, most preferably at least 8. It is also preferred that the content of tri-esterquat is less than 3 wt. %, more preferably less than 2 wt. %, most preferably less than 1 wt. %, with respect to the total weight of mono-enteramine, di-enteramine, tri-enteramine, mono-esterquat, di-esterquat, and tri-esterquat.

The weight percentages of non-quaternized tri-esteramine and quaternized tri-enteramine (as well as the weight percentages of the other species) as described herein, is determined by the quantitative analytical method described in the publication "Characterization of quaternized triethanolamine esters (esterquats) by HPLC, HRCGC and NMR", A. J. Wilkes, C. Jacobs, G. Walraven and J. M: Talbot-4th World Surfactants Congress, Barcelona, 3-7 Jun. 1996.

In another preferred embodiment, a N—$C_6$-$C_{22}$ alkyl, N-di-($C_1$-$C_3$ alkyl) amine is added to the esteramine mixture obtained after the esterification step and prior to quaternization, i.e. the quaternization is carried out in the presence of said amine. Upon quaternization, a quaternary ammonium salt mixture is obtained that contains, besides (a) the above-described esterquat, (b) a quaternary ammonium compound of formula (I)

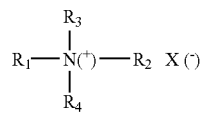

wherein, $R_1$ represents a linear or branched $C_6$-$C_{22}$ alkyl or alkenyl group, $R_2$, $R_3$, and $R_4$, independently represent a $C_1$-$C_3$ alkyl group, X represents a softener compatible anion, preferably chloride, bromide, methyl sulfate, ethyl sulfate and nitrate, more preferably chloride or methyl sulfate.

The compound (b) is preferably a N—$C_6$-$C_{22}$ alkyl, N-trimethyl ammonium chloride or N—$C_6$-$C_{22}$ alkyl, N-tri-methyl ammonium methyl sulfate. The weight ratio of the esterquat (a) to compound (b) is preferably in the range of 5:1 to 60:1, more preferably in the range of 8:1 to 50:1, most preferably in the range of 8:1 to 20:1.

Alternatively, compound (b) can also be added to the esterquat after the quaternization step in an amount as indicated above.

If compound (b) is present in the composition of the present invention, compound (b) is preferably present in an amount in the range of 1 to 20 wt %, preferably in the range of 2 to 15 wt. %, weight percentage with respect to the total weight of mono-esteramine, di-esteramine, tri-esteramine, mono-esterquat, di-esterquat, tri-esterquat, and N—$C_6$-$C_{22}$ alkyl, N-tri-($C_1$-$C_3$ alkyl) ammonium compound of formula (I).

In another preferred embodiment, a non-ionic surfactant, preferably an alkoxylated alcohol, an alkoxylated polyhydric alcohol, or mixtures thereof, is also present in the composition of the present invention (esterquat alone or esterquat in combination with compound (b)).

The alkoxylated alcohol is preferably an ethoxylated $C_6$-$C_{22}$ fatty alcohol having a linear or branched alkyl chain and having an average ethoxylation degree between 1-50, preferably between 1-30, more preferably between 1-15; or an ethoxylated linear or branched $C_7$-$C_{15}$ secondary alcohol, preferably ethoxylated linear $C_{11}$-$C_{15}$ alcohol having an average ethoxylation degree between 1-20, preferably between 1-15, more preferably 5-15.

The alkoxylated polyhydric alcohol is preferably an ethoxylated ethylene glycol, propylene glycol, 1,3-butylene glycol, 1,4-butylene glycol, dipropylene glycol, glycerol, polyglycerol, and mixtures thereof, having an average ethoxylation degree between 1-50, preferably between 1-30, more preferably between 1-15. Preferably, the alkoxylated polyhydric alcohol is ethoxylated glycerol having an average ethoxylation degree between 1-50, preferably between 1-30, more preferably between 1-15.

The Fabric Softeners

The subject matter of the present invention also includes fabric softeners comprising the composition according to the invention.

According to the invention, the quaternary ammonium salt mixture (i.e. the esterquat (a) essentially consisting of di-esteramine, tri-esteramine, mono-esterquat, di-esterquat, tri-esterquat, and solvent, and optionally non-quaternized mono-esteramine and compound (b)) is present in the fabric softeners in the range of 1 to 80% by weight, preferably from 1 to 55% by weight, even more preferably from 2 to 40% by weight, with respect to the total weight of the fabric softener.

In referring to other optional components, without this having to be regarded as an exhaustive description of all possibilities, which, on the other hand, are well known to the person skilled in the art, the following may be mentioned:

a) other products that enhance the performance of the softening compositions, such as silicones, amine oxides, anionic surfactants, such as lauryl ether sulphate or lauryl sulphate, amphoteric surfactants, such as cocoamidopropyl betaine or alkyl betaines, sulphosuccinates, polyglucoside derivatives, etc.

b) stabilising products, such as salts of amines having a short chain, which are quaternised or non-quaternised, for example of triethanolamine, N-methyldiethanolamine, etc., and also non-ionic surfactants, such as ethoxylated fatty alcohols, ethoxylated fatty amines, ethoxylated alkyl phenols, etc.

c) products that improve viscosity control, for example inorganic salts, such as calcium chloride, magnesium chloride, calcium sulphate, sodium chloride, etc.; products which can be used to reduce viscosity in concentrated compositions, such as compounds of the glycol type, such as, for example, ethylene glycol, dipropylene glycol, polyglycols, etc.; and thickening agents for diluted compositions, for example, polymers derived from cellulose, guar gum, etc.

d) components for adjusting the pH, which is preferably from 1.5 to 4.5, such as any type of inorganic and/or organic acid, for example hydrochloric, sulphuric, phosphoric, citric acid etc.

e) agents that improve soil release, such as the known polymers or copolymers based on terephthalates.

f) bactericidal preservative agents, such as formol, Kathon GC, Bronopol, etc.

g) other products such as antioxidants, colouring agents, perfumes, germicides, fungicides, anti-corrosive agents, anti-crease agents, opacifiers, optical brighteners, pearl lustre agents, etc.

The fabric softener according to the invention, may take a variety of physical forms including liquid, liquid-gel, paste-like, foam in either aqueous or non-aqueous form, powder, granular and tablet forms. For better dispersability, a preferred form of the composition is a liquid form, and in the form of an aqueous dispersion in water. When in a liquid form, the composition may also be dispensed with dispensing means such as a sprayer or aerosol dispenser.

When in a liquid form, such a fabric softener may contain from 1% to 15l; weight of a fabric softening agent, which includes the quaternary ammonium salt mixture according to the invention, in the case of standard (diluted) fabric softener but may contain higher levels from up to 30% or even 40% by weight (of the fabric softening agent, which includes the quaternary ammonium salt mixture according to the invention) in the case of very concentrated fabric softeners. The composition will usually also contain water and other additives, which may provide the balance of the composition.

Liquid fabric softeners are customarily prepared by melting the softening ingredients and adding the melt to hot water, with agitation to disperse the water-insoluble ingredients.

The fabric softener according to the invention can be used in a so-called rinse process, where a fabric softener as defined above, is first diluted in an aqueous rinse bath solution. Subsequently, the laundered fabrics which have been washed with a detergent liquor and optionally rinsed in a first inefficient rinse step ("inefficient" in the sense that residual detergent and/or soil may be carried over with the fabrics), are placed in the rinse solution with the diluted composition. Of course, the fabric softener may also be incorporated into the aqueous bath once the fabrics have been immersed therein. Following that step, agitation is applied to the fabrics in the rinse bath solution causing the suds to collapse, and residual soils and surfactant is to be removed. The fabrics can then be optionally wrung before drying.

Accordingly, there is provided a method for rinsing fabrics, which comprises the steps of contacting fabrics, previously washed in a detergent liquor, with a fabric softener according to the invention. The subject-matter of the invention also includes the use of a fabric softener of the present invention to impart fabric softness to fabrics that have been washed in a high suds detergent solution, while providing in the rinse a reduction of suds or foaming and without the creation of undesirable flocs.

This rinse process may be performed manually in basin or bucket, in a non-automated washing machine, or in an automated washing machine. When hand washing is performed, the laundered fabrics are removed from the detergent liquor and wrung out. The fabric softener of the present invention is then added to fresh water and the fabrics are then, directly or after an optional inefficient first rinse step, rinsed in the water containing the composition according to the conventional rinsing habit. The fabrics are then dried using conventional means.

The following examples are given in order to provide a person skilled in the art with a sufficiently clear and complete explanation of the present invention, but should not be considered as limiting of the essential aspects of its subject, as set out in the preceding portions of this description.

EXAMPLES

1. Synthesis of the Compositions

Esterification

The esteramine used in the examples was prepared in accordance with the following general method:

786 g of tallow fatty acid (FA) were introduced in a reactor equipped with a stirrer and a temperature probe, and 261 g of triethanolamine (TEA), 1 gram of hypophosphorous acid 50% and 0.6 grams of BHT were added with stirring. The mixture was heated at 170° C. in an inert atmosphere until the acid value was less than 5 mg KOH/g. When this value was achieved 995 grams of the reaction product, that is a complex mixture of a mono-esteramine, di-esteramine, and tri-esteramine, were obtained.

Quaternization

The compositions (esterquat or esterquat with compound (b)) of Table 1 were prepared with the use of the reagents and the quantities indicated in Table 1, in accordance with the following general method (all quantities are expressed in g):

To the esteramine described above isopropyl alcohol (IPA) and N—$C_6$-$C_{22}$ alkyl, N,N-dimethylamine (ADMA) is added with stirring and at a temperature of 55° C., dimethyl sulfate (DMS) was added dropwise over a time period of about 2 hours. The mixture maintained stirring and temperature conditions until total amine value remain constant.

The ratio tri-esteramine/tri-esterquat (EA/EQ) is also indicated in Table 1.

TABLE 1

| | | Quaternization process | | | | | | |
|---|---|---|---|---|---|---|---|---|
| | | | Quaternization process | | | | | |
| | | | | ADMA | | | Mixture obtained | |
| | | Ester amine from ester. process | $C_6$-$C_{22}$ alkyl group | Amount | IPA | DMS | Amount | Ratio EA/EQ |
| | Ex. | | | | | | | |
| Comparative Examples | 1.1 | 995 | — | — | 134 | 211 | 1340 | 0.9 |
| | 1.2 | 995 | C16 | 52.5 | 143 | 234 | 1425 | 0.9 |
| | 1.3 | 995 | C12 | 52.5 | 235 | 143 | 1425 | 0.9 |
| | 1.4 | 995 | C18 | 52.5 | 142 | 232 | 1422 | 0.9 |

TABLE 1-continued

| | | Quaternization process | | | | | | |
|---|---|---|---|---|---|---|---|---|
| | | Ester amine | ADMA C$_6$-C$_{22}$ | | | | Mixture obtained | |
| | Ex. | from ester. process | alkyl group | Amount | IPA | DMS | Amount | Ratio EA/EQ |
| According to the invention | 1.5 | 995 | C16 | 111 | 152 | 259 | 1517 | 0.9 |
| | 1.6 | 995 | C12 | 111 | 262 | 152 | 1520 | 0.9 |
| | 1.7 | 995 | C18 | 111 | 151 | 255 | 1512 | 0.9 |
| | 1.8 | 995 | — | — | 131 | 179 | 1305 | 5.4 |
| | 1.9 | 995 | C16 | 52.5 | 139 | 199 | 1386 | 5.4 |
| | 1.10 | 995 | C12 | 52.5 | 139 | 200 | 1387 | 5.4 |
| | 1.11 | 995 | C18 | 52.5 | 139 | 198 | 1385 | 5.4 |
| | 1.12 | 995 | C16 | 111 | 148 | 221 | 1475 | 5.4 |
| | 1.13 | 995 | C12 | 111 | 148 | 223 | 1477 | 5.4 |
| | 1.14 | 995 | C18 | 111 | 147 | 218 | 1471 | 5.4 |

2. Preparation of the Fabric Softener Compositions

The fabric softener compositions indicated in Table 2 and Table 3 were prepared using following procedure:

Water is heated between 40° C.-45° C. Under stirring conditions, non-ionic surfactant, is added to water. Softener base (mixtures 1.1 to 1.14 obtained in example 1) was melted and added to water, under stirring. After homogenization, formula was cooled down up to 25-30° C. Defoaming silicone emulsion was added in this point. Once was incorporated, perfume and other ingredients such us dye and preservative, were added and mixed until achieve a homogeneous composition.

For examples A1 to A7, acid was added into water after the non-ionic incorporation.

For examples C-2b and A-2b monoalkylquat (compound of formula (I)) was added into water before esterquat addition.

TABLE 2

Fabric softener compositions - comparative examples

| | C-1 | C-2a | C-2b | C-3 | C-4 | C-5 | C-6 | C-7 |
|---|---|---|---|---|---|---|---|---|
| Mixture 1.1 (esterquat) | 8 | | 7.6 | | | | | |
| Mixture 1.2 [esterquat (95%) + TriMeC16-MS[1] (5%)] | | 8 | | | | | | |
| N-cetyl-N,N,N-trimethyl ammonium chloride | | | 0.4 | | | | | |
| Mixture 1.3 [esterquat (95%) + TriMeC12-MS[2] (5%)] | | | | 8 | | | | |
| Mixture 1.4 [esterquat (95%) + TriMeC18-MS[3] (5%)] | | | | | 8 | | | |
| Mixture 1.5 [esterquat (90%) + TriMeC16-MS[1] (10%)] | | | | | | 8 | | |
| Mixture 1.6 [esterquat (90%) + TriMeC12-MS[2] (10%)] | | | | | | | 8 | |
| Mixture 1.7 [esterquat (90%) + TriMeC18-MS[3] (10%)] | | | | | | | | 8 |
| POE(20) Cetyl Stearyl Alcohol[4] | 0.2 | 0.2 | 0.2 | 0.2 | 0.2 | 0.2 | 0.2 | 0.2 |
| Silicone emulsion DC-1430 Ex Dow Corning | 0.5 | 0.5 | 0.5 | 0.5 | 0.5 | 0.5 | 0.5 | 0.5 |
| Perfume | 0.8 | 0.8 | 0.8 | 0.8 | 0.8 | 0.8 | 0.8 | 0.8 |
| Water | Balance to 100 | | | | | | | |

[1] N-cetyl-N,N,N-trimethyl ammonium methyl sulfate
[2] N-lauryl-N,N,N-trimethyl ammonium methyl sulfate
[3] N-sterayl-N,N,N-trimethyl ammonium methyl sulfate
[4] Cetyl Stearyl Alcohol having an average ethoxylation degree of 20

TABLE 3

Fabric softener compositions - according to the invention

| | A-1 | A-2a | A-2b | A-3 | A-4 | A-5 | A-6 | A-7 |
|---|---|---|---|---|---|---|---|---|
| Mixture 1.8 (esterquat) | 8.0 | | 7.6 | | | | | |
| Mixture 1.9 [esterquat (95%) + TriMeC16-MS[1] (5%)] | | 8.0 | | | | | | |
| N-cetyl-N,N,N-trimethyl ammonium chloride | | | 0.4 | | | | | |
| Mixture 1.10 [esterquat (95%) + TriMeC12-MS[2] | | | | 8.0 | | | | |

TABLE 3-continued

Fabric softener compositions - according to the invention

|  | A-1 | A-2a | A-2b | A-3 | A-4 | A-5 | A-6 | A-7 |
|---|---|---|---|---|---|---|---|---|
| (5%)] Mixture 1.11 [esterquat (95%) + TriMeC18-MS[3] (5%)] |  |  |  | 8.0 |  |  |  |  |
| Mixture 1.12 [esterquat (90%) + TriMeC16-MS[1] (10%)] |  |  |  |  | 8.0 |  |  |  |
| Mixture 1.13 [esterquat (90%) + TriMeC12-MS[2] (10%)] |  |  |  |  |  | 8.0 |  |  |
| Mixture 1.14 [esterquat (90%) + TriMeC18-MS[3] (10%)] |  |  |  |  |  |  | 8.0 |  |
| POE(20) Cetyl Stearyl Alcohol[4] | 0.2 | 0.2 | 0.2 | 0.2 | 0.2 | 0.2 | 0.2 | 0.2 |
| $H_2SO_4$ (10%) | 0.6 | 0.6 | 0.6 | 0.6 | 0.6 | 0.6 | 0.6 | 0.6 |
| Silicone emulsion DC-1430 Ex Dow Corning | 0.5 | 0.5 | 0.5 | 0.5 | 0.5 | 0.5 | 0.5 | 0.5 |
| Perfume | 0.8 | 0.8 | 0.8 | 0.8 | 0.8 | 0.8 | 0.8 | 0.8 |
| Water | Balance to 100 | | | | | | | |

[1]N-cetyl-N,N,N-trimethyl ammonium methyl sulfate
[2]N-lauryl-N,N,N-trimethyl ammonium methyl sulfate
[3]N-sterayl-N,N,N-trimethyl ammonium methyl sulfate
[4]Cetyl Stearyl Alcohol having an average ethoxylation degree of 20

3. Evaluation Methods 3.1 White Residue Evaluation 60 g of commercial powder detergent (ARIEL), was added to 8 L of water (water hardness 20° HF, French degrees of hardness, water Temperature 25° C.). Solution was stirred until complete dissolution.

Cotton terry towels (total weight 300 g) were dipped into detergent solution and maintained under movement during 1 min.

After this period towels were manually squeezed and transferred to a softener rinse bath containing 45 g of softening composition dissolved in 3 L of water (water hardness 20'HF, French degrees of hardness, water Temperature 25° C.).

Towels were maintained in the softening bath during 30 s, then were removed and manually squeezed.

After 2 minutes of towels removal, softening bath was filtered through cotton knit black fabric.

Black fabric was maintained in horizontal position until dried (room temperature), and then residue of filtration was visually assessed against a rating scale.

Effect of softener compositions reducing white residue formation is shown in Tables 4 and 5.

Notes go from 1 (poor behaviour=all black fabric surface covered by a white film residue) to 6 (excellent behaviour=black fabric surface practically free from white residues).

3.2 Softness Evaluation 30 g of commercial powder detergent (ARIEL), was added to 15 L of water (water hardness 20° HF, French degrees of hardness, water Temperature 25° C.) Solution was stirred until complete dissolution.

Cotton terry towels (total weight 1 Kg) were manually washed during 5 min.

After this period towels were manually squeezed and transferred to a softener rinse bath containing 25 g of softening composition dissolved in 20 L of water (water hardness 20° HF, French degrees of hardness, water Temperature 25° C.) during 3 min, then were removed and manually squeezed.

After drying (indoor conditions, 20° C. 65% RH), softening effect was sensorial assessed by an expert panel of 20 testers by means of a rating test using as a references:

A blank (rate 1) consisting in a towel treated in the detergent bath an then rinsed in a bath containing only water (water hardness 20° HF, French degrees of hardness, water Temperature 25° C.), and a control (rate 5) consisting in a towel previously wetted just in water (water hardness 20'HF, French degrees of hardness, water Temperature 25° C.) and then immersed in a softening bath containing 25 g of softening composition dissolved in 20 L of water (water hardness 20° HF-water Temperature 25° C.).

Softening effect is shown in Tables 4 and 5

TABLE 4

Evaluation of the fabric softener compositions - comparative examples

| | Comparative Examples | | | | | | | |
|---|---|---|---|---|---|---|---|---|
| | C-1 | C-2a | C-2b | C-3 | C-4 | C-5 | C-6 | C-7 |
| White residue (Rating from 1 to 6) | 1 | 2 | 2 | 2 | 1 | 5 | 5 | 4 |
| Softness (Rating from 1 to 5) | 4 | 4 | 4 | 4 | 4 | 3 | 3 | 3 |

TABLE 5

Evaluation of the fabric softener compositions - according to the invention

| | According to the invention | | | | | | | |
|---|---|---|---|---|---|---|---|---|
| | A-1 | A-2a | A-2b | A-3 | A-4 | A-5 | A-6 | A-7 |
| White residue (Rating from 1 to 6) | 3 | 5 | 5 | 5 | 4 | 6 | 6 | 5 |
| Softness (Rating from 1 to 5) | 4 | 4 | 4 | 4 | 4 | 3 | 3 | 3 |

From the experimental results it can be concluded that the fabric softener compositions according to the invention provide better reduction of white residues (undesirable flocs) without affecting the softness behaviour.

Particularly good results were obtained with fabric softener compositions A-2a, A2-b and A-3.

Furthermore, similar results were obtained with fabric softener composition A-2a (where the compound of formula (I) was obtained in situ with the esterquat during the quaternization process) and fabric softener composition A-2b (where the compound of formula (I) was mixed with the esterquat)

The invention claimed is:

1. A composition comprising an esterquat which is obtainable by esterification of a $C_6$-$C_{22}$ fatty acid with triethanolamine and subsequent quaternization, said mixture containing non-quaternized di-esteramine, non-quaternized tri-esteramine, quaternized mono-esteramine, quaternized di-esteramine and quaternized tri-esteramine, wherein the weight ratio of non-quaternized tri-esteramine to quaternized tri-esteramine is higher than 1.5.

2. The composition according to claim 1, wherein the weight ratio of non-quaternized tri-esteramine to quaternized tri-esteramine is higher than 5.

3. The composition according to claim 1, wherein the content of quaternized tri-esteramine is less than 3 wt. % with respect to the total amount of non-quaternized mono-esteramine~non-quaternized di-esteramine, non-quaternized tri-esteramine, quaternized mono-esteramine, quaternized di-esteramine and quaternized tri-esteramine.

4. The composition according to claim 1, further comprising (b) a quaternary ammonium compound of formula (I)

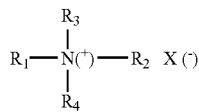

wherein,
$R_1$ represents a linear or branched $C_6$-$C_{22}$ alkyl or alkenyl group,
$R_2$, $R_3$, and $R_4$, independently represent a $C_1$-$C_3$ alkyl group,
X represents a softener compatible anion, preferably chloride, bromide, methylsulfate, ethylsulfate and nitrate, more preferably chloride or methyl sulfate.

5. A quaternary ammonium salt mixture according to claim 4, wherein the compound (b) is a N—$C_6$-$C_{22}$ alkyl, N-trimethyl ammonium chloride or N—$C_6$-$C_{22}$ alkyl, N-tri-methyl ammonium methyl sulfate.

6. The composition according to claim 4, wherein the weight ratio of the esterquat to compound (b) is in the range of 5:1 to 60:1.

7. The composition according to claim 1, further comprising a non-ionic surfactant.

8. The composition according to claim 7, wherein the non-ionic surfactant is an alkoxylated alcohol, an alkoxylated polyhydric alcohol, or mixtures thereof.

9. Process for producing the composition according to claim 1, comprising the condensation of $C_6$-$C_{22}$ fatty acids with triethanolamine providing an esteramine mixture comprising mono-esteramine, di-esteramine, and tri-esteramine, quaternization of said mixture with alkylating agents, wherein in that the molar ratio alkylating agent to esteramine ranges from 0.5 to 0.9, preferably from 0.65 to 0.85.

10. Process according to claim 9, wherein the quaternization is carried out in the presence of a N—$C_6$-$C_{22}$ alkyl, N,N-di-$C_1$-$C_3$ alkyl amine.

11. Process according to claim 9, wherein component (b) of formula (I) is mixed with the esterquat.

12. Fabric softener comprising the composition of claim 1.

13. Method for rinsing fabrics, which comprises the steps of contacting fabrics, previously washed in a detergent liquor, with a fabric softener according to claim 12.

* * * * *